United States Patent
Ismail et al.

(10) Patent No.: US 9,212,128 B2
(45) Date of Patent: Dec. 15, 2015

(54) (R)-6-(DIMETHYLAMINO)-4,4-DIPHENYLHEPTAN-3-ONE (75) Inventors: Rusli Ismail, Pulau Pinang (MY); Asaraf Ali, Pulau Pinang (MY); Soo Choon Tan, Pulau Pinang (MY)

(73) Assignee: UNIVERSITI SAINS MALAYSIA, Pulau Pinang (MY)

( * ) Notice: Subject to any disclaimer, the term of this patent is extended or adjusted under 35 U.S.C. 154(b) by 22 days.

(21) Appl. No.: 14/359,760

(22) PCT Filed: Feb. 28, 2012

(86) PCT No.: PCT/MY2012/000034
§ 371 (c)(1),
(2), (4) Date: Aug. 7, 2014

(87) PCT Pub. No.: WO2013/077720
PCT Pub. Date: May 30, 2013

(65) Prior Publication Data
US 2014/0350302 A1     Nov. 27, 2014

(30) Foreign Application Priority Data

Nov. 22, 2011  (MY) .......................... PI 2011005658

(51) Int. Cl.
| | | |
|---|---|---|
| C07C 221/00 | (2006.01) |
| C07C 223/00 | (2006.01) |
| C07C 225/00 | (2006.01) |
| C09B 11/02 | (2006.01) |
| C07C 253/30 | (2006.01) |
| C07C 253/34 | (2006.01) |
| C07C 225/16 | (2006.01) |

(52) U.S. Cl.
CPC ............. *C07C 221/00* (2013.01); *C07C 225/16* (2013.01); *C07C 253/30* (2013.01); *C07C 253/34* (2013.01); *C07B 2200/07* (2013.01)

(58) Field of Classification Search
CPC combination set(s) only.
See application file for complete search history.

(56) References Cited

U.S. PATENT DOCUMENTS 2,601,323 A    6/1952  Reid et al.

FOREIGN PATENT DOCUMENTS

WO    WO97/45551    12/1997

OTHER PUBLICATIONS

Pakkanen et al., "Methadone increases intracellular calcium in SH-SY5Y and SH-EP1-hα7 cells by activating neuronal nicotinic acetylcholine receptors" Journal of Neurochemistry, 2005, 94(5), 1329-1341.
Howe et al., "Resolution of dl-methadone and dl-isomethadone" Journal of the American Chemical Society, 1949, 71, 2935-2936.
Larsen et al., "The Resolution of Methadone and Related Compounds" Journal of the American Chemical Society, 1948, 70, 4194-4196.
Lin et al., "Syntheses of Methadone and 5-nitrofurfural" Bulletin of the Institute of Chemistry, Academia Sinica, 1980, 27, 13-17.

*Primary Examiner* — Clinton Brooks
(74) *Attorney, Agent, or Firm* — Tutunjian & Bitetto, P.C.

(57) ABSTRACT

(R)-6-(dimethylamino)-4,4-diphenylheptan-3-one and a process to produce thereof.

18 Claims, 8 Drawing Sheets

Molecules Drug Res. Laboratory
Chennai

| Sr. No. | Tests Required | Analysis |
|---|---|---|
| 1. | Description | Off white to yellow powder or flakes |
| 2. | Solubility | Soluble in methanol |
| 3. | Identification by IR | The IR spectrum of test sample should be in concordant with that of working standard. |
| 4. | Moisture content | 0.3% w/w |
| 5. | Chiral purity by HPLC | 99.8 % w/w |
| 6. | Purity by HPLC<br>1) 3-isomer content | 98.9%<br>1) 0.25% |
| 7. | Assay by HPLC | 99.7% w/w |
| 8. | Residual solvents by GC<br>1) 2-Butanol<br>2) Isopropanol | 1) 2-Butanol NMT 500 ppm<br>2) Isopropanol NMT 500 ppm |

(R)-6-(DIMETHYLAMINO)-4,4-DIPHENYLHEPTAN-3-ONE

FIELD OF INVENTION

The present invention relates to (R)-6-(dimethylamino)-4,4-diphenylheptan-3-one.

BACKGROUND OF INVENTION

Methadone is an opioid, which is widely used medically as an analgesic and an anti-addictive for use in patients with opioid dependency. Other well-known opioids used in medical treatment are hydrocodone, oxycodone and morphine. Methadone was developed by German chemists, Bockmuhl and Ehrhart, during World War II as a synthetic narcotic analgesic.

In the past, various methods have been developed to produce methadone. The method of producing methadone, also known as 6-(dimethylamino)-4,4-diphenylheptan-3-one, is disclosed in U.S. Pat. No. 4,24,274 and U.S. Pat. No. 2,601,323.

The use of methadone in medical treatment has increased over the years. However, a number of cases associated with methadone toxicities and overdose have also risen with the increase of use of methadone. Methadone confers some risk for cardiac adverse events and sudden death. Its use has been associated with arrhythmias. This effect is mediated through the ability of methadone to bind to human Etherà-go-goRelatedGene (hERG) channels in cardiacmyocytes, resulting in delayed repolarization. The risk is thought to result mainly from the use of a racemic methadone formulation that contains both (R)- and (S)-enantiomers.

The (R)-enantiomer is a mu opioid agonist responsible for therapeutic effects. The (S)-enantiomer is a poor mu agonist and can block hERG channels to a greater degree than the (R)-enantiomer, which has been postulated to be responsible for cardiac adverse events in methadone use. This information, in the context of recent studies showing a reduced effect of (R)-methadone methadone on QTc interval has generated discussion of the consideration of eliminating racemic methadone in favour of the exclusive use of (R)-methadone or buprenorphine as a means of resolving the cardiac safety issues related to current methadone treatment. A proposed solution is the use of a form of methadone that contains only the (R)-enantiomer.

Accordingly, a need still exists for a process to produce (R)-6-(dimethylamino)-4,4-diphenylheptan-3-one.

SUMMARY OF INVENTION

Accordingly, the present invention relates to (R)-6-(dimethylamino)-4,4-diphenylheptan-3-one. More particularly, the present invention provides a process to produce (R)-6-(dimethylamino)-4,4-diphenylheptan-3-one.

BRIEF DESCRIPTION OF DRAWINGS

The drawings constitute part of this specification and include an exemplary or preferred embodiment of the invention, which may be embodied in various forms. It should be understood, however, the disclosed preferred embodiments are merely exemplary of the invention. Therefore, the figures disclosed herein are not to be interpreted as limiting, but merely as the basis for the claim and for teaching one skilled in the art of the invention.

In the appended drawings.

DETAILED DESCRIPTION OF PREFERRED EMBODIMENTS

Detailed descriptions of preferred embodiments of the present invention are disclosed herein. It should be understood, however, that the embodiments are merely exemplary of the present invention, which may be embodied in various forms. Therefore, the details disclosed herein are not to be interpreted as limiting, but merely as the basis for the claim and for teaching one skilled in the art of the invention.

Particularly, the present invention relates to a process to produce (R)-6-(dimethylamino)-4,4-diphenylheptan-3-one. More particularly, the process to produce (R)-6-(dimethylamino)-4,4-diphenylheptan-3-one includes steps of preparing 4-(dimethylamino)-2,2-diphenylpentanitrile as a precursor, producing 6-(dimethylamino)-4,4-diphenylheptan-3-one and conducting resolution of 6-(dimethylamino)-4,4-diphenylheptan-3-one to produce (R)-6-(dimethylamino)-4,4-diphenylheptan-3-one.

Accordingly, first step of the process of producing (R)-methadone begins with the preparation of a precursor, 4-(dimethylamino)-2,2-diphenylpentanitrile. It is appreciated that 4-(dimethylamino)-2,2-diphenylpentanitrile is used as an intermediate in the process of producing (R)-methadone. As used herein the term methadone refers to 6-(dimethylamino)-4,4-diphenylheptan-3-one. Thus, (R)-methadone refers to (R)-6-(dimethylamino)-4,4-diphenylheptan-3-one.

The process of preparing 4-(dimethylamino)-2,2-diphenylpentanitrile is further described herein. Firstly, a charge mixture is prepared comprising a solution with a ratio containing polar aprotic solvents, a base, and an organic salt. The polar aprotic solvents are diphenylacetonitrile and dimethylformamide with a ratio preferably at 1:1. The base is preferably, but not limiting to, sodium hydroxide. The organic salt refers to aziridine salt. The charge mixture is prepared at a temperature ranging from 25° C. to 30° C.

The charge mixture is then heated at a temperature ranging from 50° C. to 55° C. to allow reaction and effect formation of 4-(dimethylamino)-2,2-diphenylpentanitrile. While heating, the charge mixture is stirred for at least 60 to 90 minutes. The reaction mixture is then allowed to cool at a temperature ranging from 25° C. to 30° C. Completion of the reaction is determined by thin layer chromatography. Extraction is then carried out with an organic solvent, preferably but not limiting to, toluene. The extraction will result in a two-phase separation layers; a basic aqueous phase and an organic phase.

Next, are efforts for recovery of 4-(dimethylamino)-2,2-diphenylpentanitrile from the reaction mixture. The organic phase is washed with demineralised water for removal of residual water-miscible impurities. The solvent is then removed preferably, but not limited to, by way of vacuum drying at a temperature ranging from 40° C. to 45° C. to leave a layer of oil which comprises of 4-(dimethylamino)-2,2-diphenylpentanitrile together with unreacted mixture. To separate the 4-(dimethylamino)-2,2-diphenylpentanitrile from the unreacted mixture, the layer of oil is dissolved in an organic solvent, preferably, but not limiting to, hexane, and stirred at a heating temperature ranging from 50° C. to 55° C. for at least 30 minutes, and followed by cooling at a temperature ranging from 40° C. to 45° C. to form solid 4-(dimethylamino)-2,2-diphenylpentanitrile. Filtration is carried out to separate the solid form 4-(dimethylamino)-2,2-diphenylpentanitrile. Afterwards, the solid is washed with an organic solvent, preferably, but not limiting to, hexane. The solvent is then removed preferably, but not limited to, by way of vacuum drying at a temperature ranging from 40° C. to 45° C. and at a pressure of 40 to 45 psi to leave pure crystalized 4-(dimethylamino)-2,2-diphenylpentanitrile.

Figure 1:
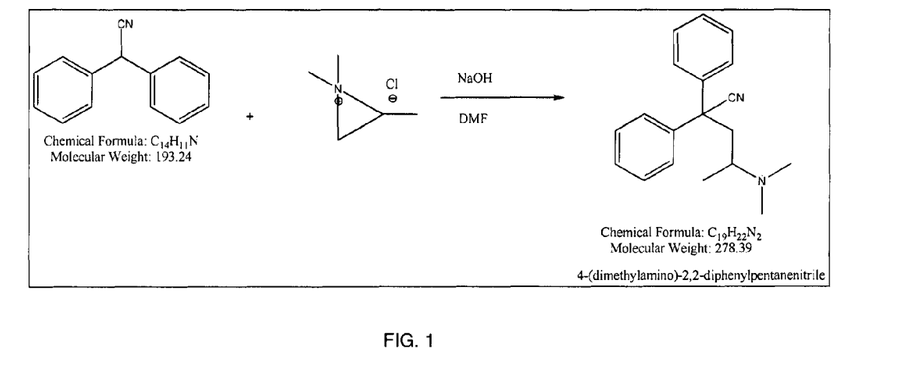
FIG. 1 illustrates the pathway of preparing 4-(dimethylamino)-2,2-diphenylpentanitrile.

FIG. 1 illustrates the pathway of preparing 4-(dimethylamino)-2,2-diphenylpentanitrile.

Typically in the second step, 4-(dimethylamino)-2,2-diphenylpentanitrile will undergo alkylation to produce a 4-(dimethylamino)-2,2-diphenylpentanitrile ethyl magnesium halide complex and then followed by hydrolysis to produce 6-(dimethylamino)-4,4-diphenylheptan-3-one. The process of producing 6-(dimethylamino)-4,4-diphenylheptan-3-one is further described herein. Firstly, a charge mixture is prepared comprising ether, an ethyl magnesium halide and a solution containing 4-(dimethylamino)-2,2-diphenylpentanitrile in xylene. The ethyl magnesium halide is preferably, but not limiting to, ethyl magnesium bromide. Preferably, but not limiting to, the ratio of 4-(dimethylamino)-2,2-diphenylpentanitrile in xylene is 1:2.

The charge mixture is then allowed to heat at a temperature ranging from 40° C. to 80° C. to allow reaction and to effect formation of 4-(dimethylamino)-2,2-diphenylpentanitrile ethyl magnesium halide complex. Distillation of solvent is carried out when the temperature reaches 80° C., followed by reflux at a temperature ranging from 110° C. to 115° C. Concentrated hydrochloric acid is then charged into the reaction mixture followed by demineralised water. The reaction mixture will effect formation of 6-(dimethylamino)-4,4-diphenylheptan-3-one. Next, distillation is carried out at 80°. The reaction mixture is then allowed to cool at a temperature ranging from 20° C. to 25° and stirred for at least 60 minutes. Filtration is carried out to separate the solid form 6-(dimethylamino)-4,4-diphenylheptan-3-one. Afterwards, the solid is washed with an acid, preferably, but not limiting to, 50% v/v hydrochloric acid. The solid is then dissolved in a solvent, preferably, but not limiting to, methanol. The solvent is then removed preferably, but not limited to, by way of vacuum drying at a temperature ranging from 50° C. to 55° C. and at a pressure of 40 to 45 psi to leave pure crystalized 6-(dimethylamino)-4,4-diphenylheptan-3-one.

Figure 2:
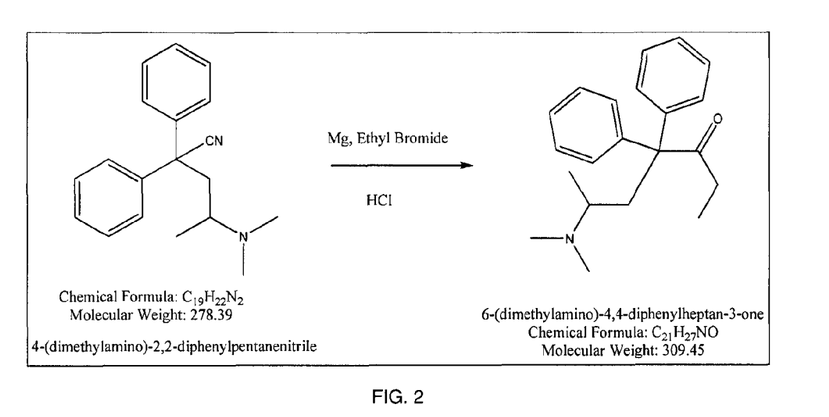
FIG. 2 illustrates a pathway of producing 6-(dimethylamino)-4,4-diphenylheptan-3-one.

FIG. 2 illustrates the pathway of producing 6-(dimethylamino)-4,4-diphenylheptan-3-one.

Final step of the process to produce (R)-6-(dimethylamino)-4,4-diphenylheptan-3-one from resolution of 6-(dimethylamino)-4,4-diphenylheptan-3-one. In another embodiment, final step of process to produce (R)-6-(dimethylamino)-4,4-diphenylheptan-3-one is described herein. A charge of mixture is prepared comprising absolute alcohol, an aliquot of demineralised water, pure crystalized 6-(dimethylamino)-4,4-diphenylheptan-3-one and a bromocamphor salt. The charge of mixture is heated up to a temperature ranging from 50° C. to 55° C. and stirred for at least 20 minutes to allow reaction and effect resolution of 6-(dimethylamino)-4,4-diphenylheptan-3-one into (R)-6-(dimethylamino)-4,4-diphenylheptan-3-one. Reaction mixture is allowed to cool at a temperature ranging from 0° C. to 5° C., stirred and filtered, followed by washing with demineralised water. Afterwards, the mother liquor is transferred to a round bottom flask. A base, preferably, but not limiting to, a 40% sodium hydroxide, is charged into the mother liquor and stirred for at least 480 minutes at a temperature ranging from 25° C. to 30° C. The mixture is allowed to cool at a temperature ranging from 5° C. to 10° C., stirred and filtered. The filtered solid is then transferred to another round bottom flask and then dissolved in a solvent, preferably, but not limiting to, acetone. The mixture is then allowed to heat up to a temperature ranging from 50° C. to 55° C., and stirred for at least 60 minutes. The mixture is then allowed to cool at a temperature ranging from 5° C. to 10° C., and stirred for at least 180 minutes. Next, filtration is then carried out to separate solid (R)-6-(dimethylamino)-4,4-diphenylheptan-3-one from the unreacted mixture and followed by washing using a solvent, preferably, but not limiting to, acetone. The solvent is then removed, preferably, but not limited to, by way of vacuum drying at a temperature ranging from 35° C. to 40° C. and at a pressure of 40 to 45 psi to leave pure crystalized (R)-6-(dimethylamino)-4,4-diphenylheptan-3-one.

Figure 3:
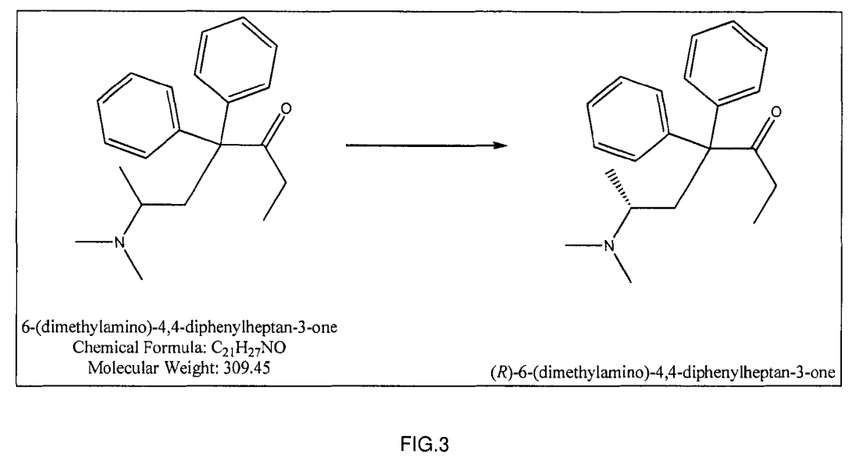
FIG. 3 illustrates the pathway of producing (R)-6-(dimethylamino)-4,4-diphenylheptan-3-one.
Figure 4A:
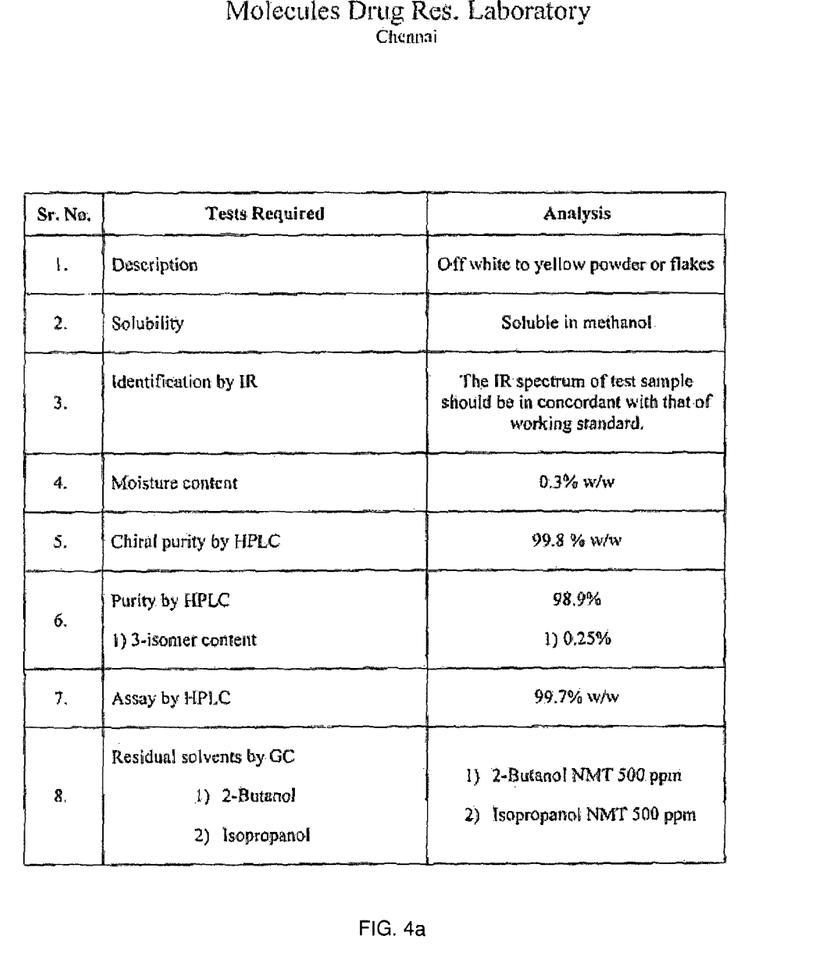
FIGS. 4a-4e illustrate Nuclear Magnetic Resonance (NMR) spectrum of (R)-6-(dimethylamino)-4,4-diphenylheptan-3-one.
Figure 4B:
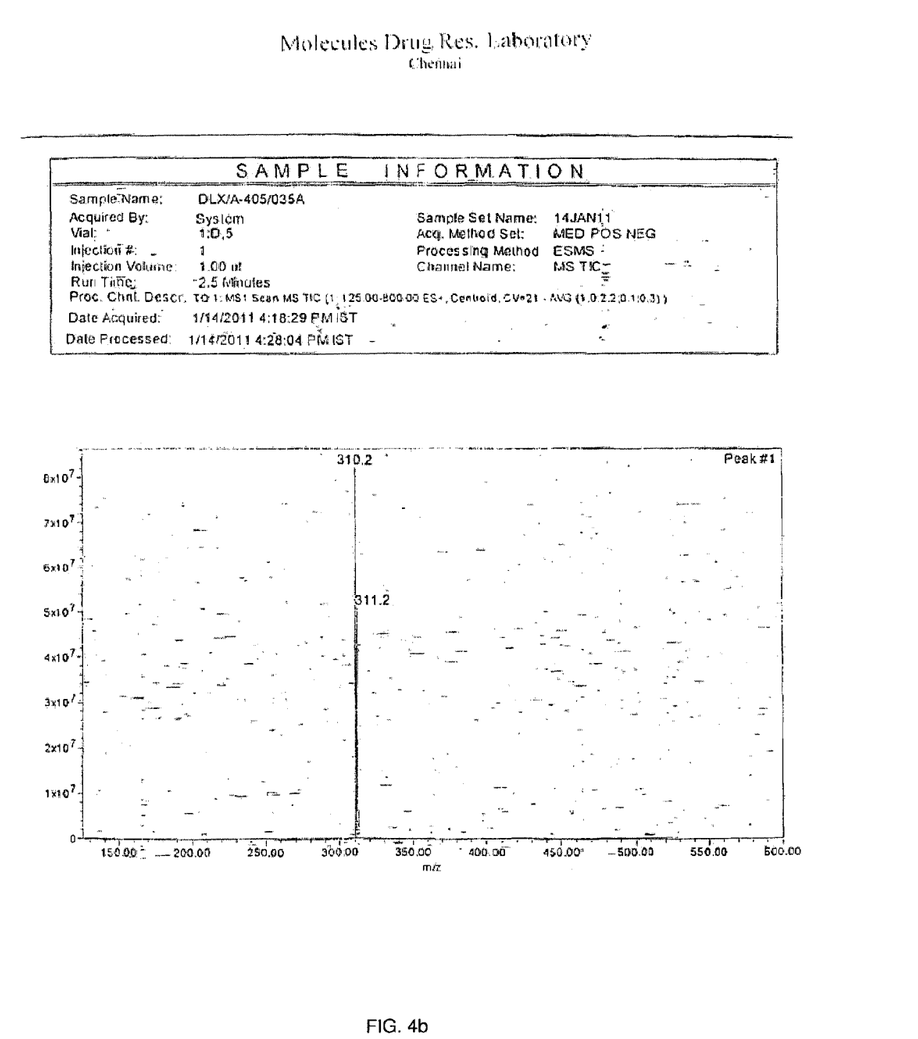
Figure 4C:
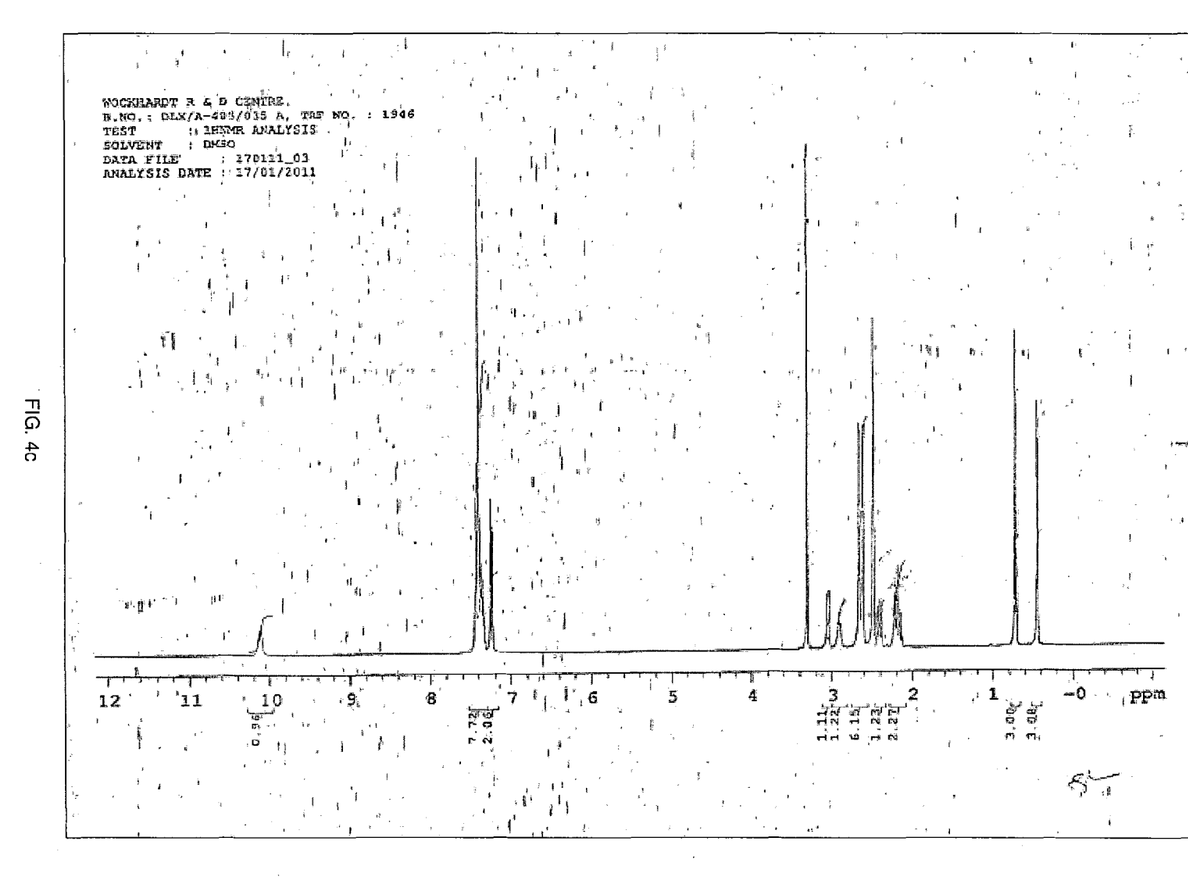
Figure 4D:
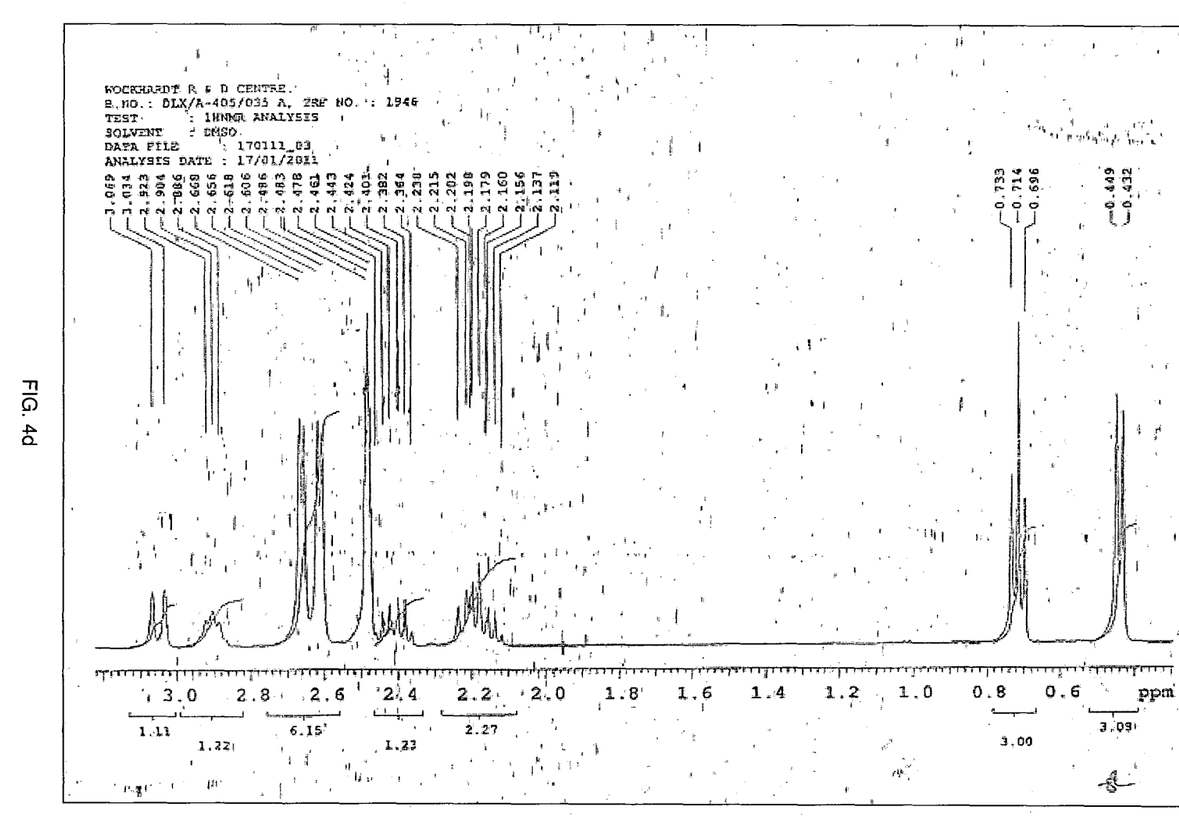
Figure 4E:
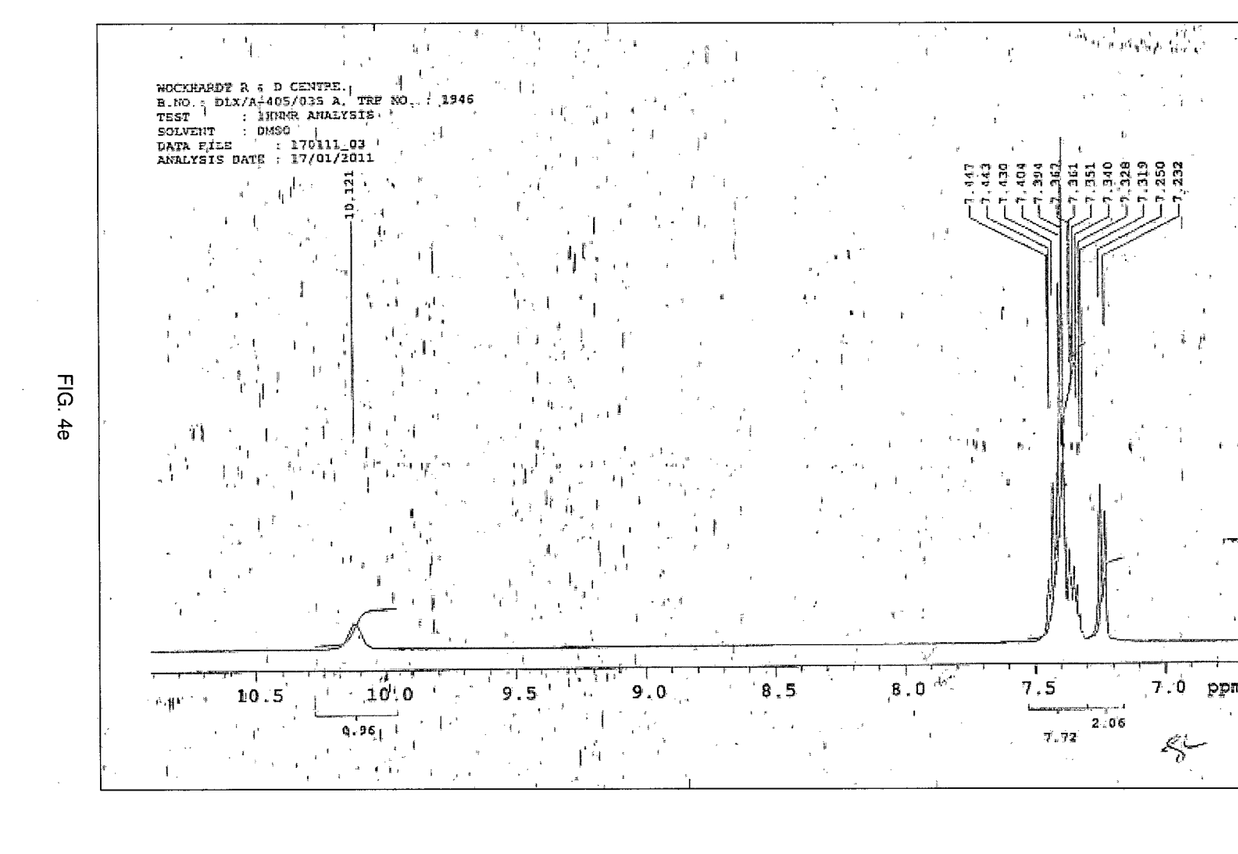

FIG. 3 illustrates the pathway to produce (R)-6-(dimethylamino)-4,4-diphenylheptan-3-one.

The following example further illustrates but by no means limits the scope of present invention:

EXAMPLE

Step 1: A Process of Preparing 4-(dimethylamino)-2,2-diphenylpentanitrile

Method:
1. Charge dry 166 ml dimethylformamide under nitrogen at room temperature ranging from 18° C. to 23° C.
2. Charge finely 22.67 gm ground sodium hydroxide at a temperature ranging from 25° C. to 30° C.
3. Mix a solution containing 100 gm diphenylacetonitrile and 134 ml dimethylformamide for at least 20-30 minutes. Continue to stir the solution for at least 30 minutes.
4. Add 68.35 gm aziridine salt.
5. Allow reaction mixture to heat up to a temperature ranging from 50° C. to 55° C. for at least 50-55 minutes. Continue to stir the mixture for at least 60-90 minutes.
6. Conduct a thin layer chromatography in 10% ethyl acetate hexane to check completion of reaction.
7. Allow to cool at a temperature ranging from 25° C. to 30° C.
8. Charge 450 ml demineralised water for at least 20-30 minutes at a temperature ranging from 20° C. to 30° C.
9. Conduct extraction with 2×700 ml toluene at a temperature ranging from 25° C. to 30° C.
10. Wash toluene with 2×350 ml demineralised water.
11. Remove solvent by distillation at a temperature ranging from 40° C. to 45° C.
12. Charge 650 ml hexane at a temperature ranging from 25° C. to 30° C.
13. Allow heating and stirring for at least 30 minutes at a temperature ranging from 50° C. to 55° C.
14. Allow to cool at a temperature ranging from 18° C. to 23° C.
15. Next, stir for at least 180 minutes.
16. Filter the solid, dry and wash with 100 ml hexane.
17. Finally, remove excess hexane and dry the solid under reduced pressure by vacuum drying at a temperature ranging from 40° C. to 45° C. and at a pressure of 40 to 45 psi Results:
Wet wt: 48.75 gm
Dry wt: 39.55 gm
Yield: 0.40 w/w

Step 2: A Process to Produce 6-(dimethylamino)-4,4-diphenylheptan-3-one

Method:
1. Charge 310 ml dry ether under room temperature ranging from 18° C. to 23° C.
2. Charge solution of ethyl magnesium bromide (prepared from 19.54 gm magnesium and 84.66 gm ethyl bromide) for at least 20-30 minutes at a temperature ranging from 25° C. to 30° C.
3. Next, charged 100 ml solution into 190 ml xylene. Mix for at least 15 minutes.
4. Remove solvent from reaction mixture by distillation at a temperature ranging from 40° C. to 80° C.
5. Conduct a reflux for at least 240 minutes at a temperature ranging from 110° C. to 115° C.
6. Next, charge 154.47 ml of concentrated hydrochloric acid at a temperature ranging from 80° C. to 90° C. Then, charge 155 ml demineralised water.
7. Remove solvent by distillation at a temperature ranging from 110° C. to 115° C.
8. Allow to cool at a temperature ranging from 18° C. to 23° C.
9. Stir for at least 60 minutes.
10. Filter the solid, wash with 1:1 hydrochloric acid (50 ml).
11. Dry the solid using vacuum pressure?
12. Add 350 ml methanol to allow re-crystallization of the solid.
13. Finally, remove excess solvent and dry the solid under reduced pressure by vacuum drying at a temperature ranging from 50° C. to 55° C. and at a pressure of 40 to 45 psi.

Results:
Wet wt: 128.38 gm
Dry wt: 110.50 gm
Yield: 1.10 w/w

Step 3: A Process to Produce (R)-6-(dimethylamino)-4,4-diphenylheptan-3-one

Method:
1. Charge 200 ml absolute alcohol under room temperature ranging from 18° C. to 23° C.
2. Charge 50 ml demineralised water at a temperature ranging from 25° C. to 30° C., then allowed to cool.
3. Next, charge 100 gm racemic compound, followed slowly by 50 gm bromocamphor salt.
4. Allow reaction mixture to heat up to a temperature ranging from 50° C. to 55° C. Continue with stirring for at least 20-30 minutes.
5. Allow to cool at a temperature ranging from 0° C. to 5° C. Stir for at least 480 minutes.
6. Next, conduct drying onto mixture, followed by washing with 50 ml demineralised water.
7. Transfer mother liquor to round bottom flask.
8. Charged 50 ml of 40% sodium hydroxide solution a temperature ranging from 25° C. to 30° C.
9. Allow to cool a temperature ranging from 5° C. to 10° C. Next, continue with stirring followed by filtration.
10. Transfer solid to round bottom flask at a temperature ranging from 20° C. to 25° C.
11. Charge 200 ml acetone a temperature ranging from 18° C. to 23° C.
12. Allow to heat up to a temperature ranging from 50° C. to 55° C. Continue to stir for at least 60 minutes.
13. Next, is cooling at a temperature ranging from 50° C. to 55° C. followed by stirring for at least 180 minutes.
14. Conduct filtration followed by washing using acetone.
15. Finally, remove excess solvent and dry the solid under reduced pressure by vacuum drying at a temperature ranging from 35° C. to 40° C. and at a pressure of 40 to 45 psi.

Results:
Wet wt: 56.79 gm
Dry wt: 43.08 gm
Yield: 0.43 w/w

While embodiments and examples of the present invention have been illustrated and described, it is not intended that these embodiments and examples illustrate and describe all possible forms of the present invention. Rather, words used in the specification are words of description rather than limitation and various changes may be made without departing from the scope of the invention.

The invention claimed is:

1. A process to produce (R)-6-(dimethylamino)-4,4-diphenylheptan-3-one wherein the process includes steps of:
   i) preparing a charge mixture comprising a solution containing polar aprotic solvents, a base, and an organic salt;
   ii) heating the charge mixture at a temperature ranging from 50° C. to 55° C. to allow reaction and effect formation of 4-(dimethylamino)-2,2-diphenylpentanitrile;
   iii) separating the 4-(dimethylamino)-2,2-diphenylpentanitrile from unreacted mixture;
   iv) dissolving the 4-(dimethylamino)-2,2-diphenylpentanitrile in an organic solvent;
   v) heating the organic solvent mixture containing 4-(dimethylamino)-2,2-diphenylpentanitrile to a temperature ranging from 50° C. to 55° C. for at least 30 minutes;
   vi) cooling at a temperature ranging from 40° C. to 45° C. to form solid 4-(dimethylamino)-2,2-diphenylpentanitrile;
   vii) conducting filtration to separate the solid form 4-(dimethylamino)-2,2-diphenylpentanitrile form the mixture;
   viii) washing the solid form 4-(dimethylamino)-2,2-diphenylpentanitrile with an organic solvent;
   ix) removing the solvent to leave pure crystalized 4-(dimethylamino)-2,2-diphenylpentanitrile;
   x) conducting alkylation of pure crystalized 4-(dimethylamino)-2,2-diphenylpentanitrile obtained in step (ix) to effect formation of 4-(dimethylamino)-2,2-diphenylpentanitrile ethyl magnesium halide complex;
   xi) conducting hydrolysis of 4-(dimethylamino)-2,2-diphenylpentanitrile ethyl magnesium halide complex obtained in step (x) to produce 6-(dimethylamino)-4,4-diphenylheptan-3-one;
   xii) mixing pure crystalized 6-(dimethylamino)-4,4-diphenylheptan-3-one obtained in step xi) with a charge of mixture comprising absolute alcohol, an aliquot of demineralised water, and a bromocamphor salt;
   xiii) heating the charge mixture to a temperature ranging from 50° C. to 55° C. to allow reaction and effect resolution of 6-(dimethylamino)-4,4-diphenylheptan-3-one into (R)-6-(dimethylamino)-4,4-diphenylheptan-3-one;
   xiv) cooling the mixture at a temperature ranging from 0° C. to 5° C.;
   xv) conducting filtration;
   xvi) washing with demineralised water;
   xvii) adding a base to the mixture;
   xviii) stirring the mixture for at least 480 minutes at a temperature ranging from 25° C. to 30° C.;
   xix) cooling the mixture at a temperature ranging from 5° C. to 10° C.;

xx) conducting filtration to separate (R)-6-(dimethylamino)-4,4-diphenylheptan-3-one from the mixture;
xxi) dissolving (R)-6-(dimethylamino)-4,4-diphenylheptan-3-one obtained in step (xx) in a solvent;
xxii) heating the solvent containing (R)-6-(dimethylamino)-4,4-diphenylheptan-3-one up to a temperature ranging from 50° C. to 55° C.;
xxiii) stirring solvent containing (R)-6-(dimethylamino)-4,4-diphenylheptan-3-one for at least 60 minutes;
xxiv) cooling solvent containing (R)-6-(dimethylamino)-4,4-diphenylheptan-3-one at a temperature ranging from 5° C. to 10° C.;
xxv) stirring the solvent containing the solid (R)-6-(dimethylamino)-4,4-diphenylheptan-3-one for at least 180 minutes to form solid (R)-6-(dimethylamino)-4,4-diphenylheptan-3-one;
xxvi) conducting filtration to separate solid (R)-6-(dimethylamino)-4,4-diphenylheptan-3-one from the unreacted mixture;
xxvii) washing the solid (R)-6-(dimethylamino)-4,4-diphenylheptan-3-one using a solvent; and
xxviii) removing the solvent to leave pure crystalized solid (R)-6-(dimethylamino)-4,4-diphenylheptan-3-one.

2. The process as claimed in claim 1 wherein the polar aprotic solvents in step (i) are diphenylacetonitrile and dimethylformamide.

3. The process as claimed in claim 1 wherein the base in step (i) is sodium hydroxide.

4. The process as claimed in claim 1 wherein the organic salt is aziridine salt.

5. The process as claimed in claim 1 wherein the organic solvent in step (iv) is hexane.

6. The process as claimed in claim 1 wherein step (vii) is conducted by vacuum drying at a temperature ranging from 40° C. to 45° C.

7. The process as claimed in claim 1 wherein step (viii) is conducted by vacuum drying at a temperature ranging from 35° C. to 40° C.

8. The process as claimed in claim 1 wherein the base in step (xvii) is 40% sodium hydroxide.

9. The process as claimed in claim 1 wherein the solvent in step (xxvii) is acetone.

10. The process as claimed in claim 2 wherein ratio of diphenylacetonitrile to dimethylformamide is 1:1.

11. The process as claimed in claim 1 wherein step (x) further includes steps of:
i) preparing a charge mixture is comprising ether, an ethyl magnesium halide and a solution containing pure crystalized 4-(dimethylamino)-2,2-diphenylpentanitrile in xylene;
ii) heating the charge mixture at a temperature ranging from 40° C. to 80° C. to allow reaction and to effect formation of 4-(dimethylamino)-2,2-diphenylpentanitrile ethyl magnesium halide complex;
iii) conducting distillation on the mixture at 80° C.; and
iv) conducting reflux at a temperature ranging from 110° C. to 115° C. to form pure 4-(dimethylamino)-2,2-diphenylpentanitrile ethyl magnesium halide complex.

12. The process as claimed in claim 8 wherein the ethyl magnesium halide is ethyl magnesium bromide.

13. The process as claimed in claim 8 wherein ratio of 4-(dimethylamino)-2,2-diphenylpentanitrile to xylene is 1:2.

14. The process as claimed in claim 1 wherein step (xi) further includes steps of:
i) preparing a charge mixture comprising of pure 4-(dimethylamino)-2,2 diphenylpentanitrile ethyl magnesium halide complex, concentrated hydrochloric acid and an aliquot of demineralised water to effect formation of 6-(dimethylamino)-4,4-diphenylheptan-3-one;
ii) conducting distillation at 80° C.;
iii) conducting cooling at a temperature ranging from 20° C. to 25° to effect formation of solid form 6-(dimethylamino)-4,4-diphenylheptan-3-one;
iv) conducting filtration to separate the solid form 6-(dimethylamino)-4,4-diphenylheptan-3-one;
v) washing the solid form 6-(dimethylamino)-4,4-diphenylheptan-3-one with an acid;
vi) dissolving the solid form 6-(dimethylamino)-4,4-diphenylheptan-3-one in a solvent; and
vii) removing the solvent to leave pure crystalized 6-(dimethylamino)-4,4 diphenylheptan-3-one.

15. The process as claimed in claim 11 wherein the acid in step (v) is 50% v/v hydrochloric acid.

16. The process as claimed in claim 11 wherein the solvent is methanol.

17. The process as claimed in claim 11 wherein step (vii) is conducted by vacuum drying at a temperature ranging from 50° C. to 55° C.

18. A process to produce (R)-6-(dimethylamino)-4,4-diphenylheptan-3-one wherein the process includes steps of:
i) preparing a charge mixture is comprising ether, an ethyl magnesium halide and a solution containing pure crystalized 4-(dimethylamino)-2,2-diphenylpentanitrile in xylene;
ii) heating the charge mixture at a temperature ranging from 40° C. to 80° C. to allow reaction and to effect formation of 4-(dimethylamino)-2,2-diphenylpentanitrile ethyl magnesium halide complex;
iii) conducting distillation on the mixture at 80° C.;
iv) conducting reflux at a temperature ranging from 110° C. to 115° C. to form pure 4-(dimethylamino)-2,2-diphenylpentanitrile ethyl magnesium halide complex;
v) mixing the 4-(dimethylamino)-2,2diphenylpentanitrile ethyl magnesium halide complex with a charge mixture comprising concentrated hydrochloric acid and an aliquot of demineralised water to effect formation of 6-(dimethylamino)-4,4-diphenylheptan-3-one;
vi) conducting distillation at 80° C.;
vii) conducting cooling at a temperature ranging from 20° C. to 25° C. to effect formation of solid form 6-(dimethylamino)-4,4-diphenylheptan-3-one;
viii) conducting filtration to separate the solid form 6-(dimethylamino)-4,4-diphenylheptan-3-one;
ix) washing the solid form 6-(dimethylamino)-4,4-diphenylheptan-3-one with an acid;
x) dissolving the solid form 6-(dimethylamino)-4,4-diphenylheptan-3-one in a solvent;
xi) removing the solvent to leave pure crystalized 6-(dimethylamino)-4,4diphenylheptan-3-one;
xii) mixing pure crystalized 6-(dimethylamino)-4,4-diphenylheptan-3-one with a charge of mixture comprising absolute alcohol, an aliquot of demineralised water, and a bromocamphor salt;
xiii) heating the charge mixture to a temperature ranging from 50° C. to 55° C. to allow reaction and effect resolution of 6-(dimethylamino)-4,4-diphenylheptan-3-one into (R)-6-(dimethylamino)-4,4-diphenylheptan-3-one;
xiv) cooling the mixture at a temperature ranging from 0° C. to 5° C.;
xv) conducting filtration;
xvi) washing with demineralised water;
xvii) adding a base to the mixture;
xviii) stirring the mixture for at least 480 minutes at a temperature ranging from 25° C. to 30° C.;

xix) cooling the mixture at a temperature ranging from 5° C. to 10° C.;
xx) conducting filtration to separate (R)-6-(dimethylamino)-4,4-diphenylheptan-3-one from the mixture;
xxi) dissolving (R)-6-(dimethylamino)-4,4-diphenylheptan-3-one obtained in step in a solvent;
xxii) heating the solvent containing (R)-6-(dimethylamino)-4,4-diphenylheptan-3-one up to a temperature ranging from 50° C. to 55° C.;
xxiii) stirring solvent containing (R)-6-(dimethylamino)-4,4-diphenylheptan-3-one for at least 60 minutes;
xxiv) cooling solvent containing (R)-6-(dimethylamino)-4,4-diphenylheptan-3-one at a temperature ranging from 5° C. to 10° C.;
xxv) stirring the solvent containing (R)-6-(dimethylamino)-4,4-diphenylheptan-3-one for at least 180 minutes to form solid (R)-6-(dimethylamino)-4,4-diphenylheptan-3-one;
xxvi) conducting filtration to separate solid (R)-6-(dimethylamino)-4,4-diphenylheptan-3-one from the unreacted mixture;
xxvii) washing the solid (R)-6-(dimethylamino)-4,4-diphenylheptan-3-one using a solvent; and;
xxviii) removing the solvent to leave pure crystalized solid (R)-6-(dimethylamino)-4,4-diphenylheptan-3-one.

\* \* \* \* \*